US008808688B2

(12) United States Patent
Yamamoto et al.

(10) Patent No.: US 8,808,688 B2
(45) Date of Patent: Aug. 19, 2014

(54) CELL PREPARATION FOR ERECTILE DYSFUNCTION OR SENSORY DISORDERS OF THE LOWER URINARY TRACT CONTAINING ADIPOSE TISSUE DERIVED MESENCHYMAL STEM CELLS

(75) Inventors: Tokunori Yamamoto, Nagoya (JP); Naoshi Koide, Nagoya (JP); Yoshifumi Takei, Nagoya (JP); Yoshihisa Matsukawa, Nagoya (JP); Yasuhito Funahashi, Nagoya (JP); Momokazu Gotoh, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 15 days.

(21) Appl. No.: 13/500,484

(22) PCT Filed: Sep. 7, 2010

(86) PCT No.: PCT/JP2010/065271
§ 371 (c)(1),
(2), (4) Date: Jun. 7, 2012

(87) PCT Pub. No.: WO2011/043147
PCT Pub. Date: Apr. 14, 2011

(65) Prior Publication Data
US 2012/0244130 A1    Sep. 27, 2012

(30) Foreign Application Priority Data

Oct. 6, 2009  (JP) ................................ 2009-232068
Mar. 12, 2010  (JP) ................................ 2010-056522

(51) Int. Cl.
*C12N 5/07* (2010.01)
*C12N 5/071* (2010.01)

(52) U.S. Cl.
CPC ............ *C12N 5/0653* (2013.01); *C12N 5/0667* (2013.01); *C12N 5/06* (2013.01)
USPC ...................................................... 424/93.7

(58) Field of Classification Search
CPC ....... C12N 5/06; C12N 5/0653; C12N 5/0667
USPC ...................................................... 424/93.7
See application file for complete search history.

(56) References Cited

U.S. PATENT DOCUMENTS

| 8,372,797 B2 * | 2/2013 | Ichim ................................ 514/1 |
| 2010/0092432 A1 | 4/2010 | Ozaki et al. |
| 2011/0059052 A1 * | 3/2011 | Ra et al. ........................ 424/93.7 |

FOREIGN PATENT DOCUMENTS

| EP | 1788079 A1 | 5/2007 |
| WO | WO 2007/149548 * | 12/2007 |
| WO | WO-2007/149548 A2 | 12/2007 |
| WO | WO-2008/018450 A1 | 2/2008 |
| WO | WO 2009 069991 * | 6/2009 |
| WO | WO-2009/120879 A1 | 10/2009 |

OTHER PUBLICATIONS

"First Patient Treated in Adipose Stem & Regenerative Cell Study for Stress Urinary Incontinence", Cytori, Jan. 30, 2009, XP002694355, 2 sheets.
Furuta, Akira et al.: "State of the art of where we are at using stem cells for stress urinary Incontinence", Neurourology and Urodynamics 2007, vol. 26, No. 7, 2007, pp. 966-971.
Smaldone, M C et al., "Stem cell therapy for urethral sphincter regeneration", Minerva Urologica E Nefrologica 2009 Edizioni Minerva Medica S.P.A. ITA, vol. 61, No. 1, Mar. 2009, pp. 27-40.
Daniels, E, "Cytori Therapeutics, Inc", Regenerative Medicine 200705 GB, vol. 2, No. 3, May 2007, pp. 317-320.
Supplementary European Search Report dated Apr. 19, 2013, issued for the corresponding European patent application No. 10821818.1.
Dennis N. Smith et al., "Collagen Injection Therapy for Post-Prostatectomy Incontinence," J. of Urology, 1998, vol. 160, No. 2, pp. 364-367.
Marc C. Smaldone et al., "Muscle derived stem cell therapy for stress urinary incontinence," World J. of Urology, 2008, vol. 26, No. 4, pp. 327-332.
Gregory S. Jack et al., "Processed Lipoaspirate Cells for Tissue Engineering of the Lower Urinary Tract: Implications for the Treatment of Stress Urinary Incontinence and Bladder Reconstruction," J. of Urology, 2005, vol. 174, No. 5, pp. 2041-2045.
Thomas M. Fandel et al., "The Effect of Adipose Tissue-Derived Stem Cells in the Preservation of Erectile Function After Cavernous Nerve Crush Injury in Aged Rats," J. of Urology, 2009, vol. 181, No. 4, p. 44.
Maurice M. Garcia et al., "Adipose-Derived Stem Cells for the Treatment of Diabetic Erectile Dysfunction in the ZDF Type-II Diabetic Fatty Rat," J. of Urology, 2009, vol. 181, No. 4, p. 44.
Guiting Lin et al., "Potential of Adipose-Derived Stem Cells for Treatment of Erectile Dysfunction," J. of Sexual Medicine, 2009, vol. 6, pp. 320-327.
International Search Report dated Nov. 9, 2010, issued for PCT/JP2010/065271.

* cited by examiner

*Primary Examiner* — Ruth Davis
(74) *Attorney, Agent, or Firm* — Edwards Wildman Palmer LLP

(57) ABSTRACT

An object is to provide a novel medical use of adipose tissue-derived mesenchymal stem cells. It was discovered that adipose tissue-derived mesenchymal stem cells (ASC) promote improvement of erectile dysfunction and recovery of the urge to urinate (improvement of sensory disorders of the lower urinary tract). On the basis of the discovery, a cell preparation containing adipose tissue-derived mesenchymal stem cells, which is effective to erectile dysfunction or sensory disorders of the lower urinary tract, is provided. In one embodiment, adipose tissue-derived mesenchymal stem cells and body fat are used in combination.

3 Claims, 23 Drawing Sheets

Fig.1
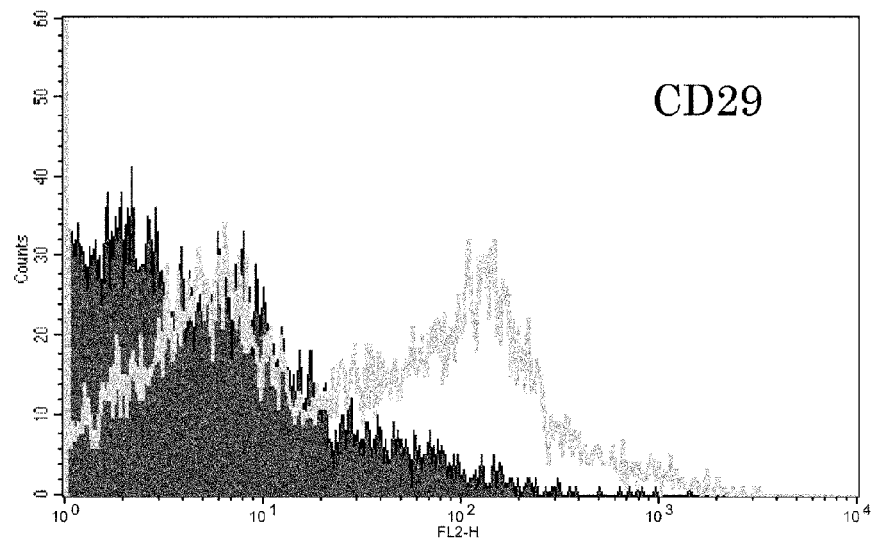
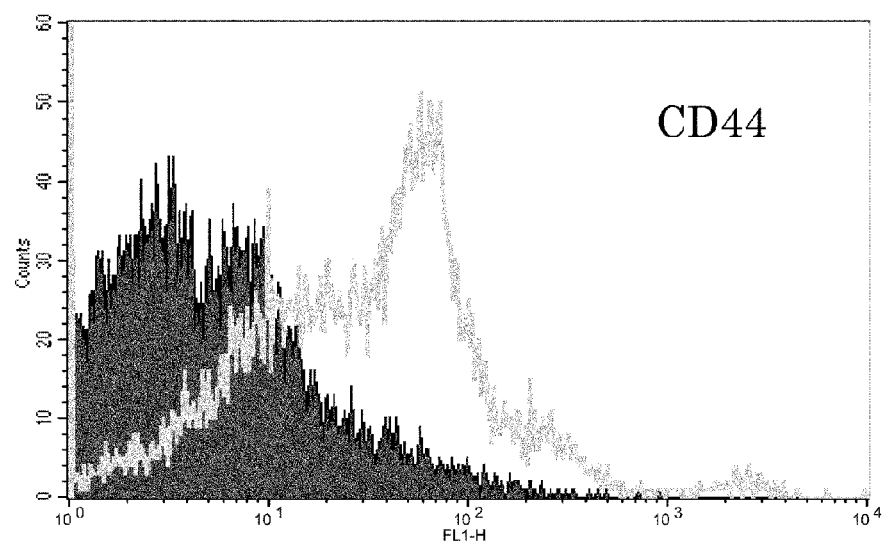

Primary culture (Day 4)     Fat differentiation (Day 7)

Fig.4

A. Blood flow in periurethral zone (periurethral zone/pelvic floor muscle group contrast effect)

| Cases | pre-operation | post-operation | After one month | After two months | After three months |
|---|---|---|---|---|---|
| 1 | 4.01 | 7.14 | 4.10 | 4.75 | 6.50 |
| 2 | 7.23 | 7.49 | 1.67 | 8.26 | 5.23 |
| 3 | 5.7 | 9.12 | 5.87 | 6.59 | 7.26 |
| 4 | 8.15 | 9.03 | 5.64 | 4.74 | 5.1 |
| 5 | 4.16 | 4.39 | 6.26 | 2.35 | 7.1 |

B. Single urination amount

| Cases | pre-operation | post-operation | After one month | After two months | After three months |
|---|---|---|---|---|---|
| 1 | 110 | 150 | 260.00 | 260.00 | 260.00 |
| 2 | 120 | 130 | 250.00 | 250.00 | 250 |
| 3 | 80 | 110 | 180 | 180 | 200.00 |
| 4 | 120 | 180 | 50 | 50 | 50 |
| 5 | 110 | 130 | 150 | 170.00 | 230.00 |

C. Amount of urinary incontinence/day

| Cases | pre-operation | post-operation | After one month | After two months | After three months |
|---|---|---|---|---|---|
| 1 | 48 | 37 | 30.00 | 10.00 | 0.00 |
| 2 | 58 | 10 | 20.00 | 15.00 | 8.00 |
| 3 | 400 | 600 | 610 | 480 | 410.00 |
| 4 | 80 | 180 | 580 | 800 | 460 |
| 5 | 110 | 130 | 120 | 80.00 | 50.00 |

Fig.11

Appearance of the urge to urinate

| Cases | pre-operation | post-operation | After one month | After two months | After three months |
|---|---|---|---|---|---|
| 1 | None | None | Sensitive | Sensitive | Sensitive |
| 2 | None | None | None | Sensitive | Sensitive |
| 3 | None | None | None | None | Sensitive |
| 4 | None | None | None | None | None |
| 5 | None | None | None | Sensitive | Sensitive |

Fig.12

EHS scores

| Cases | pre-operation | After 2 weeks | After 4 weeks | After 8 weeks | After 12 weeks | After 24 weeks |
|---|---|---|---|---|---|---|
| 1 | 0 | 0 | 0 | 1 | 2 | 2 |
| 2 | 0 | 0 | 1 | 1 | 1 | 2 |
| 3 | 0 | 0 | 0 | 0 | 1 | 1 |
| 4 | 0 | 0 | 0 | 0 | 0 | 0 |
| 5 | 0 | 1 | 1 | 1 | 1 | 1 |

Fig.13
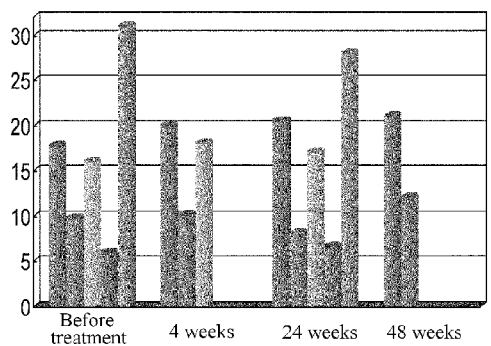
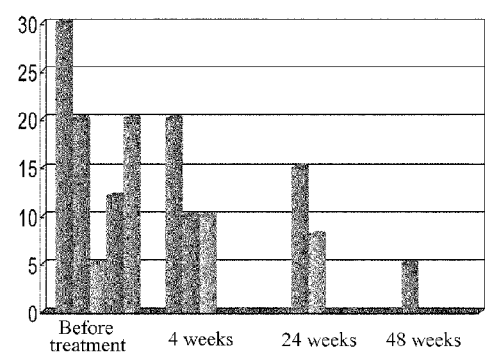

CELL PREPARATION FOR ERECTILE DYSFUNCTION OR SENSORY DISORDERS OF THE LOWER URINARY TRACT CONTAINING ADIPOSE TISSUE DERIVED MESENCHYMAL STEM CELLS

TECHNICAL FIELD

The present invention relates to a cell preparation. Specifically, the invention relates to a cell preparation effective to improvement of erectile dysfunction or sensory disorders of the lower urinary tract. The present application claims priority based on the Japanese Patent Application No. 2009-232068 filed on Oct. 16, 2009 and priority based on the Japanese Patent Application No. 2010-056522 filed on Mar. 12, 2010, and the contents of the patent applications are incorporated by reference in their entirety.

BACKGROUND ART

Stress urinary incontinence refers to a disease of leaking urine without the urge to urinate in abdominal pressures (exercise, cough, sneezing, etc.) due to functional disorder of the urethral sphincter muscle having a function that tightens the urethra in order not to leak urine from the bladder. Stress urinary incontinence is a disease shown in both males and females, and causes in a female are mainly sphincter muscle functional disorders due to pregnancy and delivery, gynecological surgeries, and aging, and causes in a male are sphincter muscle disorders due to surgeries for prostate gland enlargement and prostate gland cancer. Physical therapy (pelvic floor muscle training) is usually carried out in an early stage of a treatment for stress urinary incontinence, but is invalid in a case of having a moderate or severer symptom. As a surgical treatment, the urethral sling surgery (that is a vaginal operation, in which an artificial tape is placed under the urethra to hold the urethra) is generally broadly performed for female stress urinary incontinence and favorable results have been attained, but the urethral sling surgery has a defect such that a foreign material is left inside the body and, for male stress urinary incontinence, there is no effective surgical treatment that can be domestically performed. For a minimally invasive surgical treatment, a treatment of injecting bovine collagen into the periurethral zone (an endoscope is transurethrally inserted and collagen is injected to the membranous urethra through an endoscope) is carried out in some cases, but a treatment continuing effect is not attained because of recurrence within 1 to 3 months due to being absorbed within several weeks after the injection, and also for stress urinary incontinence after a prostate gland operation, an effectiveness itself is not more than 20%, which is defective (Non-patent Document 1). What is more, since collagen is derived from a bovine tissue, there is a problem that a risk of development of transferable spongiform encephalopathy cannot be completely denied.

The disease has a very high prevalence rate and impairs quality of life, and there is no minimally invasive, highly effective therapeutic method, and therefore, there is an urgent need to develop a minimally invasive, highly effective therapeutic method. The urethral injection treatment using cultured autologous skeletal muscle-derived stem cells has been already clinically applied to a treatment for stress urinary incontinence abroad (Non-patent Document 2), but because of difficulty of securing cultured cells to be used in injection (culture method, environment) and safety problems, development of a new noninvasive surgical therapeutic method and clinical introduction have been demanded.

A stress urinary incontinence treatment using adipose tissue-derived mesenchymal stem cells (called Adipose-derived stem cells: ASC, Adipose-derived regeneration cells: ADRC, Adipose-derived mesenchymal stem cells: AT-MSC, AD-MSC, etc.) has not been performed in Japan and abroad. It was reported that ASC is injected into the periurethral zone of a rat to differentiate to a smooth muscle (Non-patent Document 3), but no functional data showing improvement of stress urinary incontinence has been shown. The research group of the present inventors reported in the patent applications mentioned above that cultured ASC is injected into the periurethral zone using a stress urinary incontinent rat model to thus obtain increase of a urethral internal pressure and improvement of urinary incontinence (Patent Document 1).

PRIOR ART DOCUMENT

Patent Document

Patent Document 1: WO No. 2008/018450

Non-Patent Document

Non-patent Document 1: Smith D N, Appell R A, Rackley R R, Winters JCCOLLAGEN INJECTION THERAPY FOR POST-PROSTATECTOMY INCONTINENCE J Urol. 1998 August; 160(2): 364-7.
Non-patent Document 2: Smaldone M C, Chancellor M B. Muscle derived stem cell therapy for stress urinary incontinence. World J Urol. 2008 August; 26(4): 327-32. Epub 2008 May 10.
Non-patent Document 3: Jack G S, Almeida F G, Zhang R, Alfonso Z C, Zuk P A, Rodriguez L V. Processed lipoaspirate cells for tissue engineering of the lower urinary tract: implications for the treatment of stress urinary incontinence and bladder reconstruction. J Urol. 2005 November; 174(5): 2041-5.

SUMMARY OF THE INVENTION

Problems to be Solved by the Invention

An object of the present invention is to provide a novel medical use of adipose tissue-derived mesenchymal stem cells (ASC).

Means for Solving the Problem

The present inventors conducted a research to develop a new treatment for stress urinary incontinence using autologous ASC obtained from subcutaneous adipose tissues as a cell source, that is, to develop a treatment of ASC periurethral injection through the urethra under an endoscope, as an initial purpose. Firstly, a cell injection method into the periurethral zone was studied as a preliminary experiment. Specifically, a relationship between a ratio of adipose tissues and ASC separated from adipose tissues in mixing the both to be injected and the effect of lower urinary obstruction (bulking effect) was examined. As a result, when the ratio was set to 1:10 (the case of the maximum ratio of ASC in this experiment), the largest effect of lower urinary obstruction was observed and it was revealed that enhancing a mixing ratio of ASC gives a preferable effect. Subsequently, therapeutic effects of ASC were examined according to the following procedure on male patients having stress urinary incontinence due to urethral sphincter muscle disorder and showing no improvement with conventional treatments (patients who experienced radical prostate gland extirpation for prostate gland cancers or transurethral prostate gland excision for prostate-gland enlargement) as subjects. For each patient, 250-300 g of adipose tissues were collected from the lower abdominal wall or buttocks with a fat suction device and a thick cell solution containing a necessary amount of adipose tissue-derived mesenchymal stem cells was prepared using an adipose tissue-derived mesenchymal stem cell separation device. Then, a part of the thick cell solution was injected into the urethral sphincter muscle under observation with an endoscope inserted through the urethra. Subsequently, the collected residual thick cell solution and autologous adipose tissues were mixed and injected to the membranous urethra transurethrally (injection was continued until the bladder neck is occluded with swelling). After the operation, various examinations and questionnaires were periodically conducted. As a result, increase of blood flow in the periurethral zone, increase of a single urination amount, and decrease of a urinary incontinence amount were observed in many patients. That is, improvement of symptoms of urinary incontinence by ASC transplantation was confirmed. On the other hand, surprisingly, appearance of the urge to urinate was observed in one of the patients after 1 month from the operation, and appearance of the urge to urinate was observed even in 4 out of 5 patients after 3 months from the operation. Furthermore, as a more interesting result, improvement of erectile dysfunction (ED) was observed even in 4 out of 5 patients. Recovery of the urge to urinate and improvement of erectile dysfunction dramatically enhance quality of lives of patients having urinary incontinence, and the above mentioned finding has an extremely important clinical meaning.

According to the above description, as a result of studies made by the present inventors, findings which were never expected at first, that is, improvement of the urge to urinate due to ASC transplantation and improvement of erectile dysfunction, were attained. On the other hand, as a result of carrying out an animal experiment in order to evaluate characteristics of ASC after transplantation, it was revealed that ASC was differentiated to smooth muscle cells. In addition, the fact that ASC produces HGF (stem cell growth factor), which is supposed to relate to urethral sphincter muscle regrowth and differentiation and have an important role and the fact that a HGF concentration increases only in an early stage of regeneration to guarantee safety were confirmed. What is more, also according to a transplantation experiment using a large animal (pig) as a subject, effectiveness and safety of a treatment using ASC were shown. The present inventions shown below are based on the above mentioned findings.

[1] A cell preparation for erectile dysfunction or sensory disorders of the lower urinary tract, containing adipose tissue-derived mesenchymal stem cells.

[2] The cell preparation according to [1], further containing body fat.

[3] The cell preparation according to [2], which is a kit constituted with a primary element containing adipose tissue-derived mesenchymal stem cells and a secondary element containing body fat separated from a living body.

[4] The cell preparation according to [2], containing adipose tissue-derived mesenchymal stem cells, wherein body fat separated from a living body is administered in combination when the cell preparation is administered.

[5] The cell preparation according to any one of [1] to [4], wherein the adipose tissue-derived mesenchymal stem cells are cell surface marker CD29 and CD44 positive.

[6] The cell preparation according to any one of [1] to [4], wherein the adipose tissue-derived mesenchymal stem cells are (1) adhesive cells or their passaged cells, which are contained in a sedimented cell population sedimented when a cell population separated from adipose tissues is subjected to centrifugation under the conditions at 800-1500 rpm for 1-10 minutes, (2) cells which are proliferated when the sedimented cell population is cultured under the low-serum condition, (3) cells which are proliferated when a cell population separated from adipose tissues is cultured under the low-serum condition, (4) a sedimented cell population which is obtained by treating adipose tissues with protease, thereafter subjecting to a filtration treatment, and then centrifuging the filtrate to be recovered as sediments, or (5) a sedimented cell population which is obtained by treating adipose tissues with protease, and then centrifuging the treated adipose tissues to be recovered as a sediments without undergoing a filtration treatment.

[7] The cell preparation according to [6], wherein the low-serum condition is a condition that a serum concentration in a culture solution is not more than 5% (V/V).

[8] The cell preparation according to any one of [1] to [7], wherein the adipose tissues are human adipose tissues.

[9] A method for preparing a cell preparation for erectile dysfunction or sensory disorders of the lower urinary tract, including the following steps:

(1) a step of preparing adipose tissue-derived mesenchymal stem cells and body fat; and (2) a step of mixing the adipose tissue-derived mesenchymal stem cells and the body fat.

[10] A use of adipose tissue-derived mesenchymal stem cells for producing a cell preparation for erectile dysfunction or sensory disorders of the lower urinary tract.

[11] A use of adipose tissue-derived mesenchymal stem cells and body fat, for producing a cell preparation for erectile dysfunction or sensory disorders of the lower urinary tract.

[12] A method of treating erectile dysfunction or sensory disorders of the lower urinary tract, including administering the cell preparation according to [8] to the external urethral sphincter muscle and/or to the membranous urethra of external urethral sphincter muscle of a patient suffering from erectile dysfunction or sensory disorders of the lower urinary tract.

[13] A method of treating erectile dysfunction or sensory disorders of the lower urinary tract, including administering a therapeutically effective amount of adipose tissue-derived mesenchymal stem cells to the external urethral sphincter muscle and/or to the membranous urethra of external urethral sphincter muscle of a patient suffering from erectile dysfunction or sensory disorders of the lower urinary tract.

[14] A method of treating erectile dysfunction or sensory disorders of the lower urinary tract, including administering therapeutically effective amounts of adipose tissue-derived mesenchymal stem cells and body fat to the external urethral sphincter muscle and/or to the membranous urethra of external urethral sphincter muscle of a patient suffering from erectile dysfunction or sensory disorders of the lower urinary tract.

BRIEF DESCRIPTION OF THE DRAWINGS

FIG. 1 shows results of measuring cell surface markers of cells, which were prepared from adipose tissues. It is found to be CD29 and CD44 positive.

FIG. 4 is a table showing a blood flow in the periurethral zone (A), a single urination amount (B) and a urinary incontinence amount/day (C) of each patient before and after the treatment.

FIG. 11 is a table showing presence or absence of appearance of the urge to urinate before and after a treatment for each patient.

FIG. 12 is a table showing EHS scores before and after a treatment for each patient. 0: The penis is not larger, 1: the penis is larger but not hard, 2: the penis is hard but not hard enough for penetration, 3: the penis is hard enough for penetration but not completely hard, 4: the penis is completely hard and fully rigid.

FIG. 13 is a graph showing change of urination states before and after an operation. The graph shows changes of maximum urine flow rates (left) and residual urine amounts (right) (cases 1, 2, 3, 4, and 5 in order from the left). In every case, the maximum urine flow rate does not decrease (that is, the urination state does not deteriorate), and increase of residual urine is not observed. That is, the urination (urinary excretion) function is not damaged.

DESCRIPTION OF EMBODIMENTS

Figure 2:
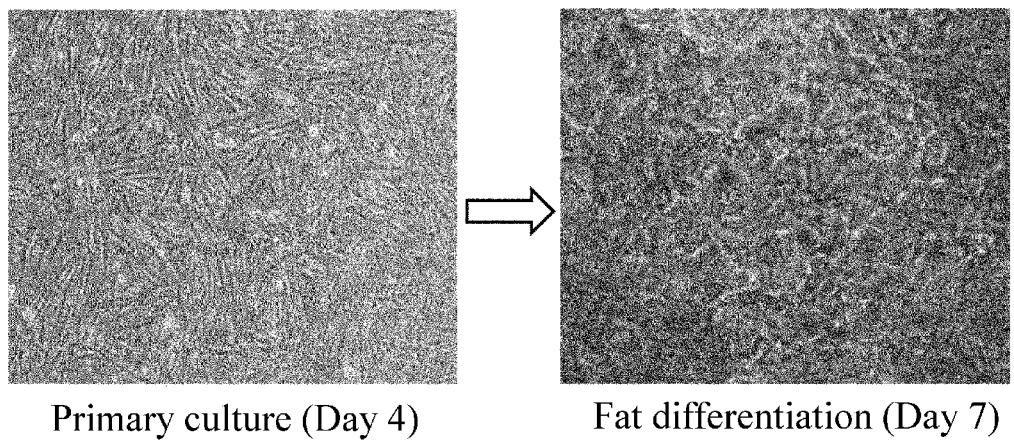
FIG. 2 shows results of culturing cells which were prepared from adipose tissues. The cells were cultured in an adipose differentiation medium to induce differentiation.

The present invention relates to a cell preparation applied to a specific disease and a use thereof. The cell preparation of the present invention contains adipose tissue-derived mesenchymal stem cells (also may be abbreviated as "ASC" in the specification). "The adipose tissue-derived mesenchymal stem cells (ASC)" in the present invention refers to somatic stem cells that are contained in an adipose tissue, and cells that are obtained by culture of the somatic stem cells (including subculture) also correspond to "the adipose tissue-derived mesenchymal stem cells (ASC)" as long as such cells maintain multipotency. Generally, ASC is obtained from an adipose tissue separated from a living body as a starting material, and prepared into "an isolated state" as a cell that constitutes a cell population (containing cells except for ASC, which are originated from the adipose tissue). "An isolated state" herein means that ASC is present in a state of being taken out from its original environment (that is, a state of constituting a part of a living body), in other words, a state of being different from an original state of its existence due to artificial manipulation. Note that adipose tissue-derived mesenchymal stem cells are also called ADRC (adipose-derived regeneration cells), AT- MSC (adipose-derived mesenchymal stem cells), AD-MSC (adipose-derived mesenchymal stem cells), and so on. In the present specification, the following terms, that is, adipose tissue-derived mesenchymal stem cells, ASC, ADRC, AT-MSC, and AD-MSC are used exchangeably.

(Preparation Method of ASC)

ASC is prepared through steps such as separation of stem cells from a fat substrate, washing, concentration, and culture. A preparation method of ASC is not particularly limited. For example, ASC can be prepared according to, for example, known methods (Fraser J K et al. (2006), Fat tissue: an underappreciated source of stem cells for biotechnology. Trends in Biotechnology; April; 24(4): 150-4. Epub 2006 Feb. 20. Review.; Zuk P A et al. (2002), Human adipose tissue is a source of multipotent stem cells. Molecular Biology of the Cell; December; 13(12): 4279-95.; Zuk P A et al. (2001), Multilineage cells from human adipose tissue: implications for cell-based therapies. Tissue Engineering; April; 7(2): 211-28., and the like are served as references). Further, a device for preparing ASC from adipose tissues (for example, Celution (registered trademark) device (Cytori Therapeutics, Inc., USA, San Diego)) is also commercially available and ASC may be prepared using the device. When the device is used, cells that are cell surface marker CD29 and CD44 positive can be separated from adipose tissues. Specific examples of a preparation method of ASC are shown below.

(1) Preparation of Population of Cells from Adipose Tissue

Adipose tissue can be obtained from an animal by means such as excision and suck. The term "animal" herein includes human and non-human mammalians (pet animals, domestic animal, and experimental animal. Specifically examples include mouse, rat, guinea pig, hamster, monkey, cow, pig, goat, sheep, dog, cat, and the like). In order to avoid the problem of immunological rejection, it is preferable that adipose tissue is collected from the same individuals as subjects (recipients) to which the cell preparation of the present invention is to be administered. However, adipose tissue of the same kinds of animals (other animals) or adipose tissue heterogeneous animals may be used.

An example of adipose tissue can include subcutaneous fat, offal fat, intramuscular fat, and inter-muscular fat. Among them, subcutaneous fat is a preferable cell source because it can be collected under local anesthesia in an extremely simple and easy manner and therefore the burden to a patient in collection is small. In general, one kind of adipose tissue is used, but two kinds or more of adipose tissues can be used. Furthermore, adipose tissues (which may not be the same kind of adipose tissue) collected in a plurality of times may be mixed and used in the later operation. The collection amount of adipose tissue can be determined by considering the kind of donors or kinds of tissue, or the necessary amount of ASCs. For example, the amount can be from 0.5 g-500 g. When a donor is human, it is preferable that the collection amount at one time is about 10 g-20 g or less by considering a burden to the donor. The collected adipose tissue is subjected to removal of blood components attached thereto and stripping if necessary and thereafter, subjected to the following enzyme treatment. Note here that by washing adipose tissue with appropriate buffer solution or culture solution, blood components can be removed.

The enzyme treatment is carried out by digesting adipose tissue with protease such as collagenase, trypsin and Dispase. Such an enzyme treatment may be carried out by techniques and conditions that are known to a person skilled in the art (see, for example, R.I. Freshney, Culture of Animal Cells: A Manual of Basic Technique, 4th Edition, A John Wiley & Sones Inc., Publication). Preferably, enzyme treatment is carried out by the bellow-mentioned techniques and conditions. A cell population obtained by the above-mentioned enzyme treatment includes multipotent stem cells, endothelial cells, interstitial cells, blood corpuscle cells, and/or precursor cells thereof. The kinds or ratios of the cells constituting the cell population depend upon the origin and kinds of adipose tissue to be used.

(2) Obtaining of Sedimented Cell Population (SVF Fraction: Stromal Vascular Fractions)

The cell population is then subjected to centrifugation. Sediments obtained by centrifugation are collected as sedimented cell population (also referred to as "SVF fraction" in this specification). The conditions of centrifugation are different depending upon the kinds or amount of cells. The centrifugation is carried out for example, at 800-1500 rpm for 1-10 minutes. Prior to the centrifugation, cell population after enzyme treatment can be subjected to filtration and tissue that has not been digested with enzyme contained therein can be removed.

The "SVF fraction" obtained herein includes ASCs. Therefore, the cell preparation of the present invention can be prepared using the SVF fraction. That is, the SVF fraction is contained in one embodiment of the cell preparation of the present invention. The kinds or ratio of cells constituting the SVF fraction depend upon the origin and kinds of adipose tissue to be used, conditions of the enzyme treatment, and the like. The SVF fraction is characterized by including CD34 positive and CD45 negative cell population, and that CD34 positive and CD45 negative cell population (International Publication WO2006/006692A1).

(3) Selective Culture of Adhesive Cells (ASC) and Recovery of Cells

Other cell components (such as endothelial cells, stroma cells, hematopoietic cells, and precursor cells thereof) are contained in a SVF fraction other than ASC. Thus, in one embodiment of the present invention, unnecessary cell components are removed from the SVF fraction by carrying out the following selective culture. Then, cells that are obtained as a result are used in the cell preparation of the present invention as ASC.

Firstly, a SVF fraction is suspended in an appropriate medium, and then seeded on a culture dish and cultured overnight. Floating cells (non-adhesive cells) are removed by replacement of a medium. Then, culture is continued while suitable replacement of a medium (for example, once per 3 days). Subculture is carried out according to necessity. The passage number is not particularly limited. Note that, for the culture medium, a medium for normal animal cell culture can be used. Examples such as Dulbecco's modified Eagle's Medium (DMEM) (NISSUI PHARMACEUTICAL, etc.), α-MEM (Dainippon Seiyaku, etc.), DMED: Ham's F12 mixed medium (1:1) (Dainippon Seiyaku, etc.), Ham's F12 medium (Dainippon Seiyaku, etc.), and MCDB 201 medium (Research Institute for the Functional Peptides) can be used. Media added with serums (fetal bovine serum, human serum, sheep serum, etc.) or serum replacement s (Knockout serum replacement (KSR), etc.) may also be used. The adding amount of a serum or serum replacement can be set within the range from 5% (v/v)-30% (v/v), for example.

Adhesive cells selectively survive and proliferate according to the above mentioned operations. Next, the cells proliferated are collected. The cells may be collected by routine procedures and, for example, collected easily by enzyme treatment (treatment with trypsin or Dispase) and then cells are scraped out by using a cell scraper, a pipette, or the like. Furthermore, when sheet culture is carried out by using a commercially available temperature sensitive culture dish, cells may be collected in a sheet shape without carrying out enzyme treatment. Use of thus collected cells (ASC) makes it possible to prepare a cell preparation containing ASC at high purity.

(4) Low-Serum Culture (Selective Culture in a Low-Serum Medium) and Collection of Cells In one embodiment of the present invention, the following low-serum culture is carried out in place of or after (3) mentioned above. Then, the cells obtained as a result are used as ASC in the cell preparation of the present invention.

In low-serum culture, the SVF fraction (when this step is carried out after (3), the cells that are collected in (3) are used) is cultured under the low-serum conditions and a desired multipotent stem cell (that is, ASC) is selectively proliferated. Since the amount of serum to be used is small in the low-serum culture method, it is possible to use the serum of the subjects (recipients) themselves to which the cell preparation of the present invention is administered. That is to say, culture using autoserum can be carried. By using autoserum, it is possible to provide a cell preparation capable of excluding heterogeneous animal materials from manufacturing process and being expected to have high safety and high therapeutic effect. The "under low-serum conditions" herein denotes conditions in which a medium contains not more than 5% serum. Preferably, the sedimented cell population is cultured in a culture solution containing not more than 2% (V/V) serum. More preferably, the cells are cultured in a culture solution containing not more than 2% (V/V) serum and 1-100 ng/ml of fibroblast growth factor –2.

The serum is not limited to fetal bovine serum. Human serum, sheep serum, and the like, can be used. Preferably, the human serum, more preferably the serum of a subject to whom the cell preparation of the present invention is to be administered (that is to say, autoserum) is used.

As the medium, a medium for culturing animal cells can be used on condition that the amount of serum contained in the use is low. For example, Dulbecco's modified Eagle's Medium (DMEM) (NISSUI PHARMACEUTICAL, etc.), α-MEM (Dainippon Seiyaku, etc.), DMED:Ham's:F12 mixed medium (1:1) (Dainippon Seiyaku etc.), Ham's F12 medium (Dainippon Seiyaku, etc.), MCDB201 medium (Research Institute for the Functional Peptides), and the like, can be used.

By culturing by the above-mentioned method, multipotent stem cells (ASCs) can be selectively proliferated. Furthermore, since the multipotent stem cells (ASCs) proliferated in the above-mentioned culture conditions have a high proliferation activity, it is possible to easily prepare cells necessary in number for the cell preparation of the present invention by subculture. Note here that cells selectively proliferated by low-serum culture of SVF fraction is CD13, CD90 and CD105 positive and CD31, CD34, CD45, CD106 and CD117 negative (International Publication WO2006/006692A1).

Subsequently, selectively proliferated cells by the above-mentioned low-serum culture are collected. A collection operation may be carried out in the same manner as in the case of (3). Use of thus collected cells (ASC) makes it possible to prepare a cell preparation containing ASC at high purity.

(5) Formulation

Cells of a SVF fraction, cells obtained as a result of the above-mentioned selective culture (3), or cells obtained as a result of the above-mentioned low-serum culture (4) are suspended into physiological serine, an appropriate buffer solution (for example, phosphoric acid buffer solution), or the like and the cell preparation can be thus obtained. For example, $1 \times 10^6$-$1 \times 10^{10}$ cells may be contained as an amount of single administration so that a pharmaceutically effective amount of cells is administered. A content of cells can be suitably adjusted by considering an intended use, objective disease, and sex, age, body weight, condition of affected area and condition of cells of a subject to be applied (recipient).

The cell preparation of the present invention may include, for example, dimethylsulfoxide (DMSO), serum albumin, and the like, for protecting the cells; antibiotic and the like for inhibiting contamination of bacteria; various components (vitamins, cytokines, growth factors steroids and the like) for activation, proliferation or differentiation of cells. Examples of cytokines include interleukin (IL), interferon (IFN), colony stimulating factor (CSF), granulocyte-colony stimulating factor (G-CSF), and erythropoietin (EPO), and activin, oncostatin M (OSM). Note that CSF, G-CSF, EPO, and the like are also growth factors. On the other hand, examples of the growth factors include hepatocyte growth factor (HGF), basic fibroblast growth factor (bFGF, FGF2), epidermal growth factor (EGF), platelet-derived growth factor (PDGF), insulin-like growth factor (IGF), transforming growth factor (TGF), nerve growth factor (NGF) and brain-derived neurotrophic factor (BDNF). Furthermore, the cell preparation of the present invention may contain pharmaceutically acceptable other components (for example, carrier, excipient, disintegrating agents, buffer, emulsifier, suspension, soothing agent, stabilizer, preservatives, antiseptic, physiologic saline, etc.).

In the above-mentioned method, the cell preparation is formed by using cells proliferated by low-serum culture of SVF fraction. However, the cell preparation may be directly formed by the low-serum culture of cell population obtained from adipose tissue (without carrying out centrifugation for obtaining SVF fraction). That is to say, in one embodiment of the present invention, cells proliferated by the low-serum culture of cell population obtained from adipose tissue are used as low-serum culture ASCs. A cell preparation may also be constituted by directly using a SVF fraction (containing adipose tissue-derived mesenchymal stem cells), not using multipotent stem cells that are obtained according to selective culture ((3) and (4) mentioned above). The cell preparation in this embodiment contains (a) a sedimented cell population (SVF fraction) that is collected as sediments by treating adipose tissues with protease, thereafter being subjected to a filtration treatment, and then centrifuging the filtrate, or (b) a sedimented cell population (SVF fraction) that is collected as sediments by treating adipose tissues with protease and then centrifuging the treated adipose tissues without undergoing a filtration treatment. In addition, "directly using" herein means that a SVF fraction is used as an active ingredient of the cell preparation without undergoing selective culture.

(Combination Use of ASC and Body Fat)

In one embodiment, the cell preparation of the present invention contains body fat in addition to ASC. That is, ASC and body fat that is separated from a living body are used in combination in this embodiment. For example, 10-20 g of body fat is used as an amount of single administration so that a pharmaceutically effective amount of fat is administered.

The wording of "adipose tissue-derived mesenchymal stem cells and body fat are used in combination" or "the cell preparation is obtained by using adipose tissue-derived mesenchymal stem cells and body fat in combination" means that adipose tissue-derived mesenchymal stem cells and body fat are used concomitantly. Typically, the cell preparation of the present invention is provided as a compounding agent that is obtained by mixing a cell population containing ASC and body fat. For example, the cells of the present invention are suspended into physiological serine, an appropriate buffer solution (for example, phosphoric acid buffer solution), or the like to obtain a cell suspension and body fat may be mixed into the cell suspension. An embodiment of combination use is not particularly limited to the above-mentioned example (that is, a compounding agent) and, for example, the cell preparation of the present invention can be provided in a form of a kit that is constituted with the primary element containing ASC and the secondary element containing body fat. In this case, the both elements are administered to a recipient simultaneously or after taking a predetermined interval of time. Preferably, the both elements are administered simultaneously. "Simultaneously" herein does not demand strict simultaneity. Therefore, the concept of "simultaneously" includes the case that administration of the both elements are carried out under the condition of no substantial time lag, such as administering one element and then administering the other element quickly, as a matter of course, including the case that the both elements are administered under the condition of no time lag, such as mixing the both elements and then administering the mixed elements to a recipient. On the other hand, in the case of administering one element and then administering the other element after taking a predetermined interval of time, it is preferred that a time lag is set as short as possible so that an effect of the combination use is favorably exerted. For example, after administration of one element, the other element is administered within 15 minutes, preferably within 10 minutes, and more preferably within 5 minutes.

A cell preparation containing ASC is prepared and body fat may be administered in combination at the time of administering the cell preparation. The timing of administering the cell preparation and body fat in this case is in the same manner as in the case of the embodiment of the kit mentioned above. That is, although the both elements are preferably administered simultaneously, the both elements may be administered in a predetermined time lag. Furthermore, opposite to the above-mentioned embodiment, a cell preparation containing body fat is prepared and ASC may be administered in combination at the time of administering the cell preparation. The timing of administration in this case is followed by the case of the above-mentioned embodiment.

Examples of body fat include subcutaneous fat, visceral fat, intramuscular fat, and intermuscular fat. Among them, subcutaneous fat is particularly preferable because it can be collected under local anesthesia in an extremely easy manner. A preparation method of adipose tissues is followed by the description in the section (1) mentioned above.

(Diseases to be Applied)

A disease to be treated or prevented with the cell preparation of the present invention is erectile dysfunction or sensory disorders of the lower urinary tract. In other words, the cell preparation of the present invention is used in prevention or treatment of erectile dysfunction or prevention or treatment of sensory disorders of the lower urinary tract. Therefore, the cell preparation of the present invention is generally administered to a patient suffering from erectile dysfunction (or a potential patient) or a patient suffering from sensory disorders of the lower urinary tract (or a potential patient). However, the cell preparation of the present invention also can be used for the purpose of experiments and researches to confirm and verify its effects.

"Erectile dysfunction (ED)" is one kind of male sexual functional disorders and refers to "a condition that satisfactory sexual intercourse cannot be performed since sufficient erection is not attained during sexual intercourse or sufficient erection cannot be maintained". Erectile dysfunction (hereinafter also referred to as "ED") is also called "erectile functional disorder" or "erectile disorder". ED is classified into the mild type, the moderate type, and the complete type according to its severity. Furthermore, ED is divided into the organic factor (caused by arterial sclerosis, nerve damage, etc.), the psychological factor (caused by psychological stress), and the mixed factor (generated by combining the both elements of the organic factor and the psychological factor) according to causes.

"Sensory disorders of the lower urinary tract" refers to a condition of no occurrence of the urge to urinate in need or a condition of a low degree of the urge to urinate even with occurrence of the urge to urinate. Sensory disorders of the lower urinary tract becomes a cause of urinary incontinence, urinary retention, etc. Sensory disorders of the lower urinary tract is caused by abnormality of the urinary tract, benign prostatic hypwertrophy (BPH), neurogenic bladder, and the like. Sensory disorders of the lower urinary tract may occur after an operation of total extirpation of the prostate gland or due to neurogenic bladder as aftereffects of diabetes and cerebrovascular disorder. Amelioration of sensory disorders of the lower urinary tract brings improvement of quality of life.

(Subjects to be Applied)

A subject to which the cell preparation of the present invention is administered is typically a human. However, the cell preparation can also be constituted for non-human mammalians (pet animals, domestic animals, and experimental animals, specifically including, for example, a mouse, rat, guinea pig, hamster, monkey, cow, pig, goat, sheep, dog, cat, and the like). It has been observed that ED-like symptoms are rarely shown in dogs and horses for breeding; for example, the cell preparation of the present invention can be used also in such cases.

(Administration Method)

The cell preparation of the present invention is preferably administered into an affected area by local injection. An injection site is typically the external urethral sphincter muscle or membranous urethra. The cell preparation is preferably injected into both of these two sites, and in this case, the cell preparation that does not contain adipose tissues (that is, the cell preparation containing only ASC as the essential component) may be applied to the external urethral sphincter muscle, and the cell preparation that contains adipose tissues (that is, the cell preparation containing ASC and adipose tissues as essential components) may be applied to membranous urethra. One of intentions of using the cell preparation that contains adipose tissues lies in exhibiting an effect of lower urinary obstruction by adipose tissues. Therefore, injection may be continued until the bladder neck is occluded by swelling in order to preferably exhibit an effect of lower urinary obstruction in injection to membranous urethra. An example of an administration amount (total amount) of the cell preparation is shown to be, for instance, 0.2 ml-2 ml, and preferably 1.5 ml-2 ml for application to the external urethral sphincter muscle, and for example, 2 ml-20 ml, and preferably 15 ml-20 ml (ratio of 1:10) for application to membranous urethra. Note that the cell preparation may be injected into 2 or more sites in plural times for both of the application to the external urethral sphincter muscle and the application to membranous urethra.

Administration schedule may be formed by considering a sex, age, body weight and condition of a subject (patient). The cell preparation may be administered in plural times serially or periodically, other than single administration. An administration interval in plural administrations is not particularly limited and, for example, 1 day to 1 month. The administration number is not particularly limited. Examples of the administration number are 2 to 10.

EXAMPLES

1. Study of Cell Injection Method
1-1. Method
(1) Separation of Adipose Tissue-Derived Mesenchymal Stem Cells (ASC)

Subcutaneous fat (human) was finely vacuumed with a fat suction tube after subcutaneous injection of an extracellular fluid. Then, 260 g out of 300 g of the collected adipose tissues was injected into an adipose-derived stem cell separation device (Celution (registered trademark) device) for cell separation, and then the device was operated according to the instruction for use to separate stem cells. The separated stem cells were collected from the device using a syringe. On the other hand, adipose tissues (about 20 g) for mingling with the separated stem cells were washed. Note that a disposable set is mounted in the Celution (registered trademark) device to be able to treat the adipose tissues in each case. A treatment of detaching stem cells from the fat substrate was performed by the adipose-derived stem cell separation device, and in the treatment, the stem cells were washed and concentrated after being separated. This real time treatment was performed in a closed environment for minimizing a risk of contacting with a contaminant and completed within a time of one surgical treatment.

(2) Study of Mixing Ratio of ASC and Adipose Tissues

The following test samples (2 cc each) were prepared, and each test sample was injected subcutaneously into a nude rat with a 18 G needle to compare an effect of lower urinary obstruction (bulking effect).

Test sample a: mixture of the separated stem cells and human adipose tissues in a ratio of 1:0 (that is, only adipose tissues)

Test sample b: mixture of the separated stem cells and human adipose tissues in a ratio of 1:1 (that is, stem cells collected from 1 g of adipose tissues per 1 g of adipose tissues were used)

Test sample c: mixture of the separated stem cells and human adipose tissues in a ratio of 1:10 (that is, stem cells collected from 10 g of adipose tissues per 1 g of adipose tissues were used)

1-2. Results

ASC was separated from adipose tissues for the purpose of applications to clinical cases. ASC can be collected as a solution of a cell component slightly mixed with 5 ml of erythrocytes. An ischemic ulcer was observed in the center due to decrease of the total amount of phyma and insufficient vascularization in the test sample a (only human adipose tissues). A ratio of adipose tissues and ASC to form phyma in the interior of the urethra and the most effectively provoke an effect of lower urinary obstruction was found to be 1:10.

2. Evaluation of Characteristics of Prepared ASC

Characteristics of cells prepared from human adipose tissues using the Celution (registered trademark) device were evaluated. Firstly, a sample immediately after separation of FACS was hemolyzed with addition of ammonium chloride, and then CD29 and CD44 that are mesenchymal stem cell markers were measured. As a result, the sample showed to be CD29 and CD44 positive (FIG. 1).

On the other hand, cells prepared using the Celution (registered trademark) device were cultured with an adipose differentiation medium containing insulin, dexamethasone, indomethacin, and 3-isobutyl-1-methyl-xanthine (IBMX). Primary cells showed a fibroblastic form, and on day 4, 70 to 80% of the cells became confluent. In addition, formation of fat droplet was observed on day 7 from induction of fat differentiation and stained with Oil-Red (FIG. 2). As described above, differentiation into adipose cells was confirmed.

3. Study of Therapeutic Effect of ASC

The following study was carried out in order to find new therapeutic uses of ASC collected from adipose tissues.

3-1. Method (1) Patient (Subject to be Tested)

Patients suffering from stress urinary incontinence, who visit the department of urology in the Nagoya university hospital, were subjects to be tested. All patients experienced radical prostate gland extirpation for prostate gland cancers, and have difficult cases of continuing stress urinary incontinence for 1 year or more after the operations. Ages of the patients were 73-83 years old (75.6 years old on average).

(2) Collection of Subcutaneous Adipose Tissues

A suitable amount of a mixed solution [components: physiological serine 1000 ml+1% lidocaine (xylocalne) 2 ml+0.1% adrenaline (bosmin) 1.5 ml+8.4% meylon 10 ml] was injected into patients' abdominal or gluteal subcutaneous adipose tissues under general anesthesia, or local and lumbar anesthesia to be sufficiently distended. A suspension containing adipose tissues was vacuumed with negative pressure using a special syringe usually used in the plastic surgery field. In the case of injection under lumbar anesthesia, when a patient further had algia, intravenous anesthesia was added for pain relief.

(3) Treatment of Subcutaneous Adipose Tissues (Separation of ASC)

ASC was separated and concentrated from about 250-300 g of the adipose tissues obtained above with an ASC separation device (Celution (registered trademark) device) (about $1\times10^6$-$1\times10^8$/5 ml). Firstly, the collected adipose tissues were injected into a sterilized disposable set and washed. Then, a melting treatment was carried out on the adipose tissues, and an enzyme (Celase™) which separates cells was added to carry out a digestive treatment and centrifugation of a cell suspension and washing of the enzyme were automatically performed in a closed circuit. The collection, adjustment, and transplantation were performed in an operation room in the Nagoya university hospital. The cleanliness was in the class of 100-10000, and clean environment was maintained in all procedures.

(4) Transplantation of ASC into the Periurethral Zone

Figure 3:
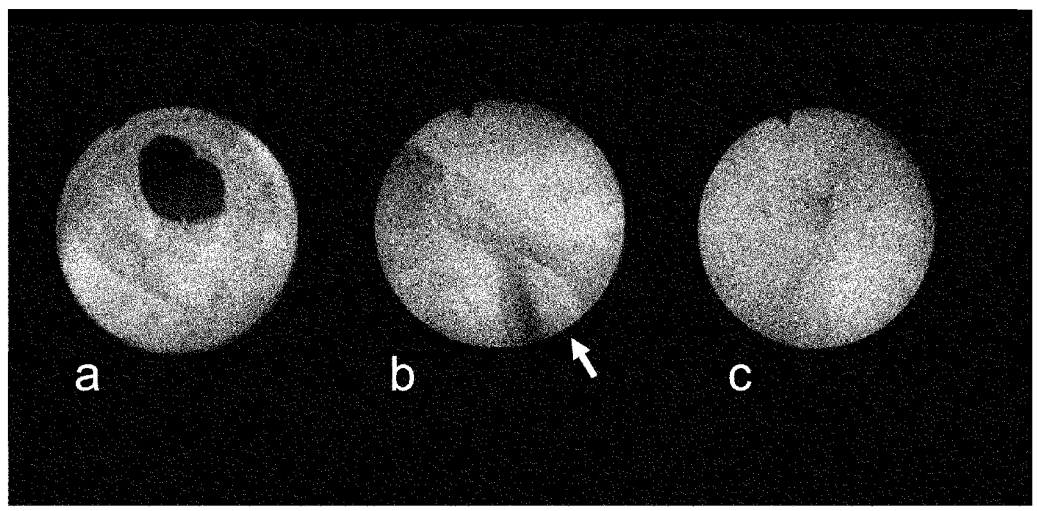
FIG. 3 is a view showing a transurethral fat/ASC injection procedure. Due to sphincter muscle disorder, the bladder neck and the urethra were opened (a), but an ASC solution is injected into the sphincter muscle, followed by injecting a mixed solution of adipose tissues and ASC to membranous urethra (b), and the urethral sphincter muscle part is adhered and occluded after the injection (c).

Two kinds of injection cell solutions, that is, (a) a cell solution with 0.5-1.0 ml of ASC and (b) a cell solution obtained by mixing 20 g of autologous fat and 4.0-4.5 ml of ASC were prepared using ASC (about $1\times10^6$-$1\times10^8$) separated into 5 ml. An endoscope was inserted from the urethra under general anesthesia, or local and lumbar anesthesia and the above mentioned 2 types of the injection cell solutions were injected into each patient using a 18 G needle injection device under the endoscope. That is, 0.5-1.0 ml of the solution (a) was injected into two sites each of the right and left sides of the external urethral sphincter muscle and the solution (b) was injected to membranous urethra (4, 8, 6 hours) according to cases in a level that occlusion of the interior of the urethra due to the effect of lower urinary obstruction (bulking effect) can be endoscopically observed (FIG. 3).

(5) Test Method and Evaluation Method

In order to examine therapeutic effects and its duration, predetermined tests (measurement of a periurethral blood flow, measurement of single urination amount, test of degree of urinary incontinence, test of urethra functions, MRI test, ultrasound examination, etc.) were carried out before a treatment, and after 2 weeks, 1 month, and 3 months from the treatment. Conditions of urinary incontinence and influence on life were also examined by a questionnaire (opinionaire). Further, an evaluation (subjective observation) by ICIQ-SF (urinary incontinence symptom/QOL score: urinary incontinence frequency, urinary incontinence amounts, and influence on daily life are evaluated in score with a self completed questionnaire whose validity has been testified), and as an objective observation, a 24-hour pad test and a urine flow dynamic test (the urethral internal pressure measurement; maximum urethral closure pressure, functional urethral length) were performed. In the 24-hour pad test, a weight of a pad was measured every time when urinary incontinence was shown (a weight of a dry pad is subtracted) and a urinary incontinence amount for 24 hours was quantitatively measured. The measurement was continued for 4 days and the mean value was calculated as a 1-day urinary incontinence amount.

3-2. Results

Figure 5:
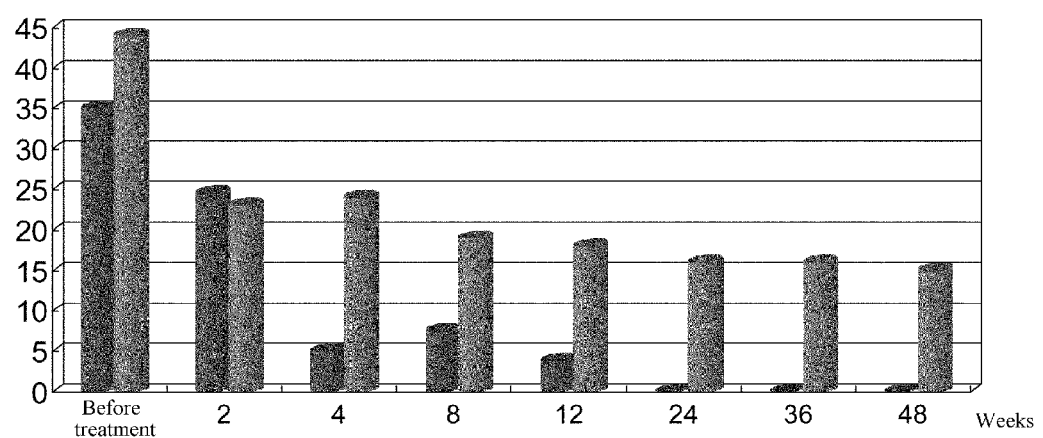
FIG. 5 is a graph showing transitions of urinary incontinence amounts of patients having cases 1 and 2 in a moderate level of urinary incontinence amounts (cases 1 and 2 in order from the left). The urinary incontinence amounts were monitored in a 24-hour pad test (evaluated with the average of continuous 3 to 4 days). Urinary incontinence disappears after 24 weeks (6 months) in the case 1.
Figure 6:
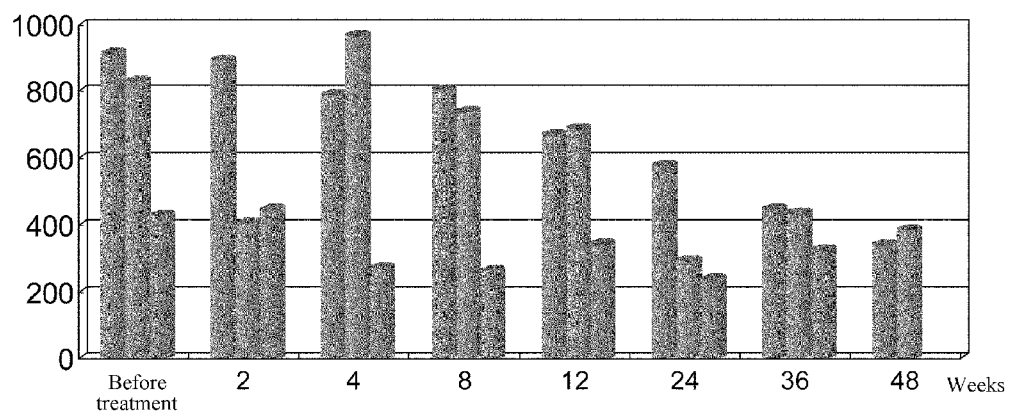
FIG. 6 is a graph showing transitions of urinary incontinence amounts of patients having cases 3, 4 and 5 in severe levels of urinary incontinence (cases 3, 4, and 5 in order from the left). The urinary incontinence amounts were monitored in a 24-hour pad test (evaluated by the average of continuous 3 to 4 days). Improvements with time of urinary incontinence amounts continue in the cases 3 and 4.
Figure 7:
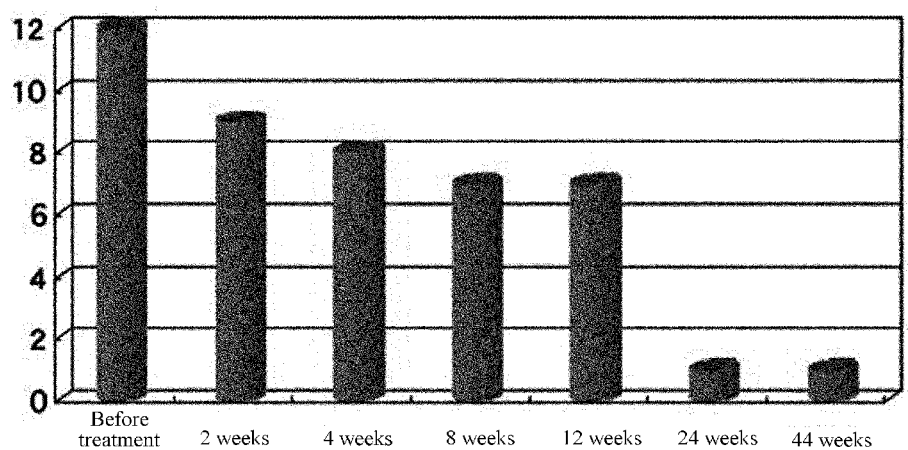
FIG. 7 is a graph showing a transition of QOL (quality of life) of the patient in the case 1. Variation of ICIQ-SF (International Consultation on Incontinence Questionnaire-Short Form), which is an international urinary incontinence symptom/QOL score, was examined.
Figure 8:
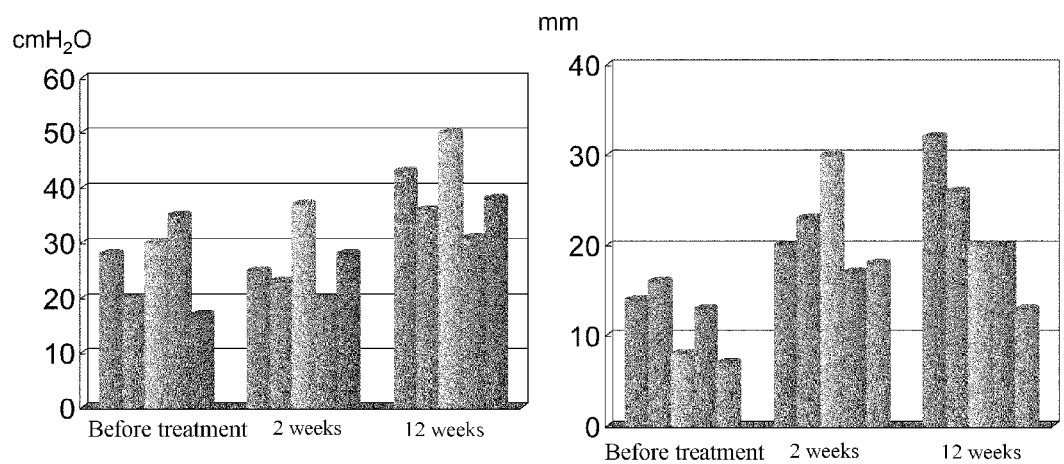
FIG. 8 is a graph showing change of urethral functions in a urethral internal pressure measurement. Left: graph showing transitions of maximum urethral closure pressures (cases 1, 2, 3, 4, and 5 in order from the left). Maximum urethral closure pressures before an operation, and after 2 weeks and 12 weeks from the operation were compared. Right: graph showing transitions of functional urethral length (cases 1, 2, 3, 4 and 5 in order from the left). Urethral sphincter muscle functions in an objective test are improved in every example. The maximum urethral closure pressure reflects a closure pressure in the sphincter muscle part, and the functional urethral length reflects the length of the sphincter muscle part.
Figure 9:
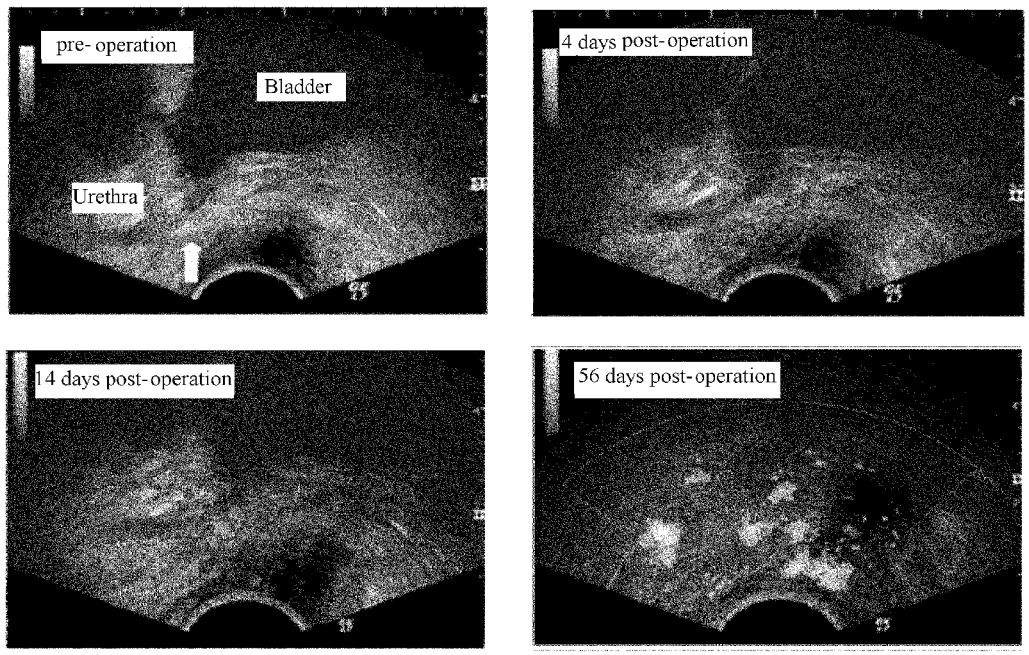
FIG. 9 shows results of ultrasonic contrast tests in injection sites (case 1). Increased blood flow with time is observed after the operation.
Figure 10:
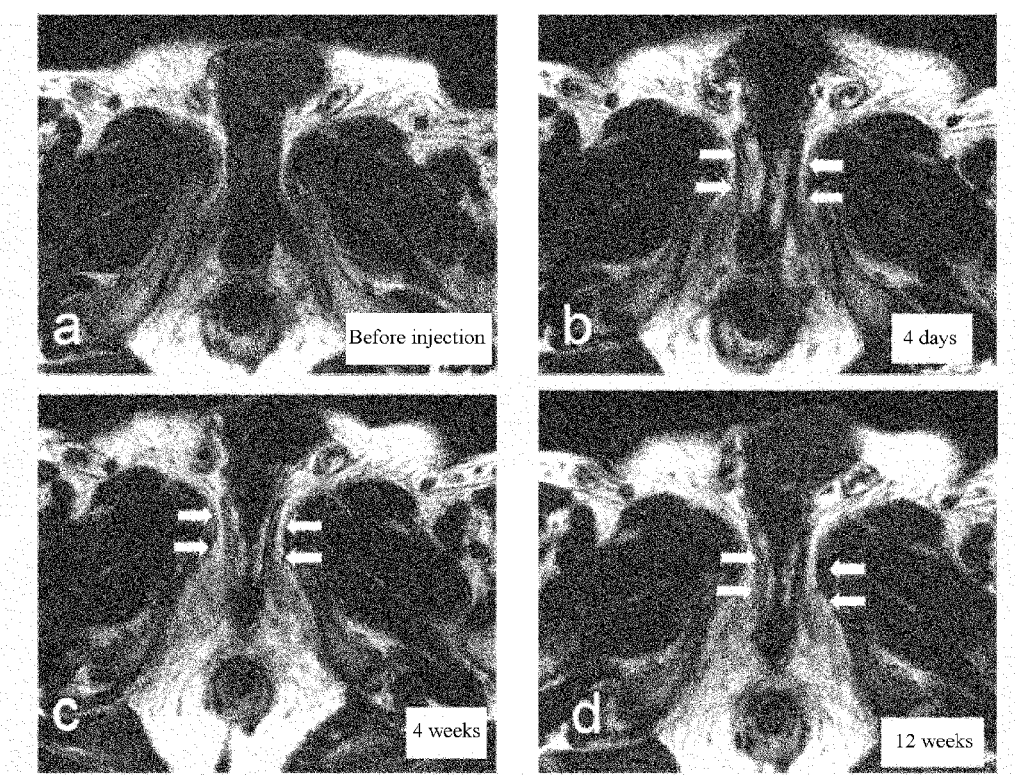
FIG. 10 shows MRI images (case 1) in the injection site. a: before injection, b: 4 days after injection, c: 4 weeks after injection, d: 12 weeks after injection. Injected autologous adipose tissues exist also at the time of passing 12 weeks after injection.

Results of each test are shown in FIGS. 4 to 12. Increase of the periurethral blood flow (the periurethral zone/pelvic floor muscle group contrast effect) is observed in most of the patients (FIG. 4A). In addition, increase of a single urination amount was observed in 4 out of 5 patients (FIG. 4B). Similarly, urinary incontinence amounts were decreased in 4 out of 5 patients (FIG. 4C). Transition of urinary incontinence amounts after operations was monitored by the 24-hour pad test for a long period of time; as a result, excellent improvement effects were observed (FIGS. 5 and 6). Further, in evaluation by ICIQ-SF, significant improvements of urinary incontinence amounts, urinary incontinence frequency, and QOL were attained (FIG. 7). In the urethral internal pressure measurement, increase of the maximum urethral closure pressures (case 1: from 28 cm $H_2O$ 20 to 43 cm $H_2O$, case 2: from 21 cm $H_2O$ 20 to 36 cm $H_2O$) (FIG. 8, left) and increase of functional urethral lengths (case 1: from 14 mm to 32 mm, case 2: from 17 mm to 27 mm) (FIG. 8, right) were observed, and improvement of urethral resistance was objectively confirmed. In the blood flow evaluation in the ADRC periurethral injection site by the contrast ultrasound examination, blood flow was increased from the next day after injection as compared to before injection, and blood flow in the injection site was increased with time by 56 days after injection (FIG. 9). Autologous adipose tissues that were injected to membranous urethra did not disappear due to absorption even at the time of 3 months after injection and continued to exist in the injection site (FIG. 10).

On the other hand, surprisingly, appearance of the urge to urinate was observed in one of the patients after 1 month from the operation (FIG. 11), and appearance of the urge to urinate was observed even in 4 out of 5 patients after 3 months from the operation. In addition, a more interesting result was obtained with respect to the index of erectile dysfunction (EHS scores). That is, improvements of erectile dysfunction were observed even in 4 out of 5 patients (FIG. 12).

As a result of examining changes of urination states before and after the operation, disorder of urination functions was not observed in all cases (FIG. 13).

As a result of transplantation of ASC, in addition to improvement of symptoms of urinary incontinence, recovery of the urge to urinate (improvement of sensory disorders of the lower urinary tract) and improvement of erectile dysfunction were observed as described above. The latter two effects are not predictable at all at first and bear mentioning. Recovery of the urge to urinate and improvement of erectile dysfunction dramatically enhance quality of life of a patient suffering from urinary incontinence. Findings of such effects caused by ASC have an extremely important clinical meaning. In particular, improvement of erectile dysfunction can be recognized as an extremely surprising effect when considering ages of patients (73 to 83 years old).

Note that, in both of two cases (cases 1 and 2) performed this time, improvements of urinary incontinence progressed with time, and particularly in the case of disappearance of urinary incontinence, urinary incontinence was progressively improved and disappeared in 24 weeks (6 months), and a significantly increased blood flow in the injection site was observed with time by the contrast ultrasound examination, and thus, improvement of the urethral sphincter muscle function is not only because of the bulking effect simply due to injection of adipose tissues, but also can be considered to deeply relate to the regeneration mechanism. Collection of subcutaneous adipose tissues can be performed in a standard minimally invasive method in a plastic surgery that is fat suction, ASC collection from adipose tissues can be safely carried out in a short time by using a separation device without requiring a culture step, and in further serial treatment procedure processes, collection of subcutaneous fat, collection of ASC, transurethral injection of collected ADRCs into the periurethral zone can be performed. Accordingly, an injection treatment of autologous ASC into the periurethral zone is a highly safe and useful clinical regeneration therapy as a new non-invasive surgical treatment for stress urinary incontinence, and is considered to have high medical significance. Stress urinary incontinence after a prostate gland operation is very intractable as compared to female stress urinary incontinence, and by considering that effectiveness was attained in two cases in this time, effectiveness of ASC to female stress urinary incontinence is also suggested.

4. Evaluation of ASC Characteristics after Transplantation

Figure 14:
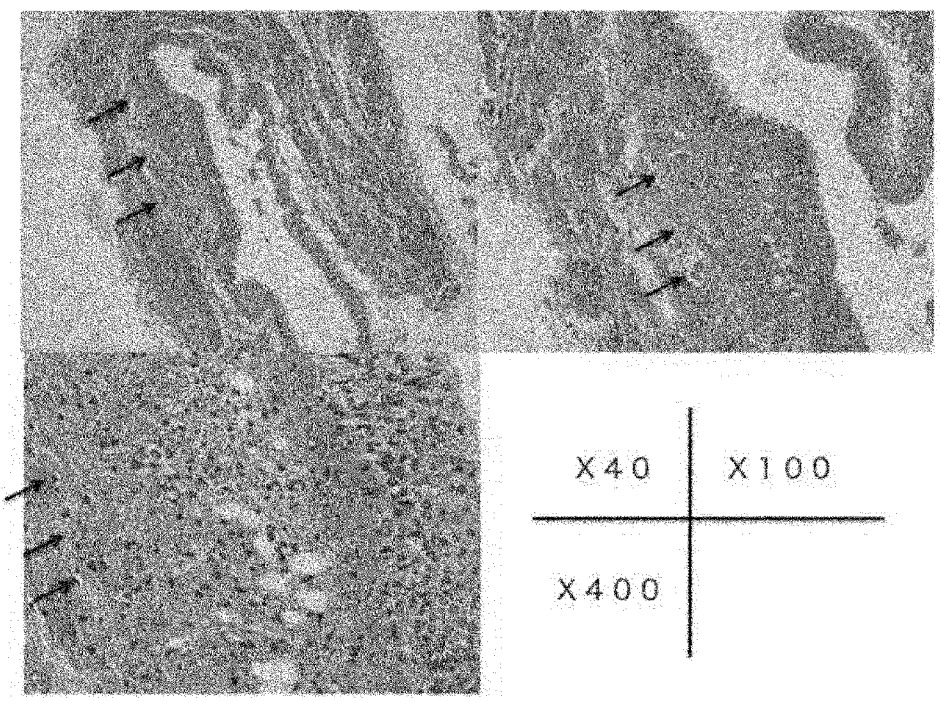
FIG. 14 shows HE (Hematoxylin Eosin) stain images of ASC injection sites (periurethral zone) of a rat. Magnifications are 40 in the left top, 200 in the right top, and 400 in the left bottom.
Figure 15:
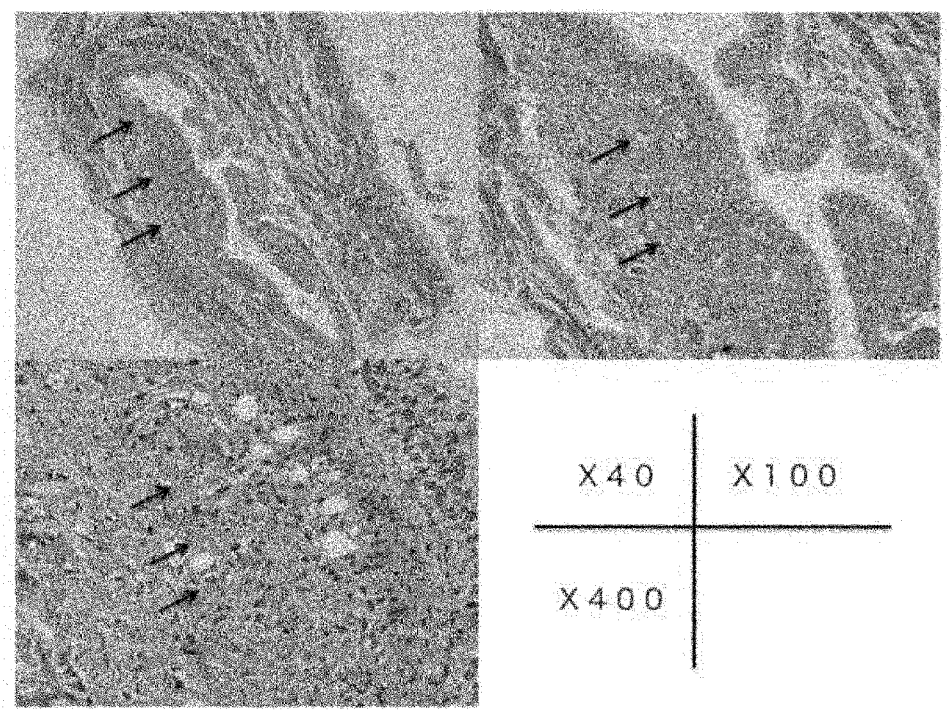
FIG. 15 shows Masson trichrome stain images of ASC injection sites (periurethral zone) of a rat. Magnifications are 40 in the left top, 200 in the right top, and 400 in the left bottom.
Figure 16:
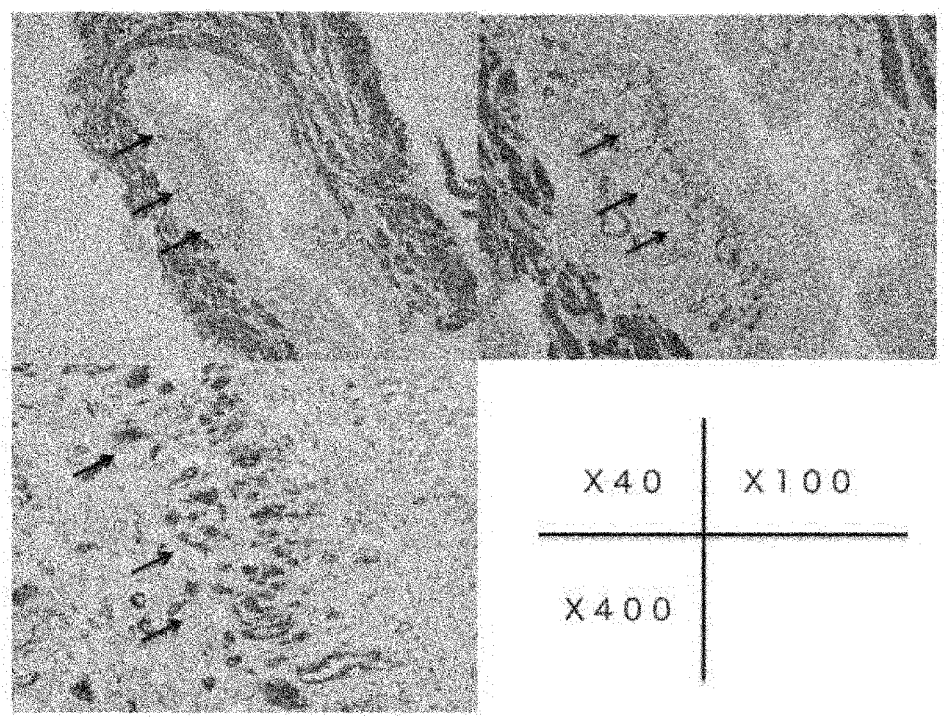
FIG. 16 shows αSMA (smooth muscle) stain images of ASC injection sites (periurethral zone) of a rat. Magnifications are 40 in the left top, 200 in the right top, and 400 in the left bottom.
Figure 17:
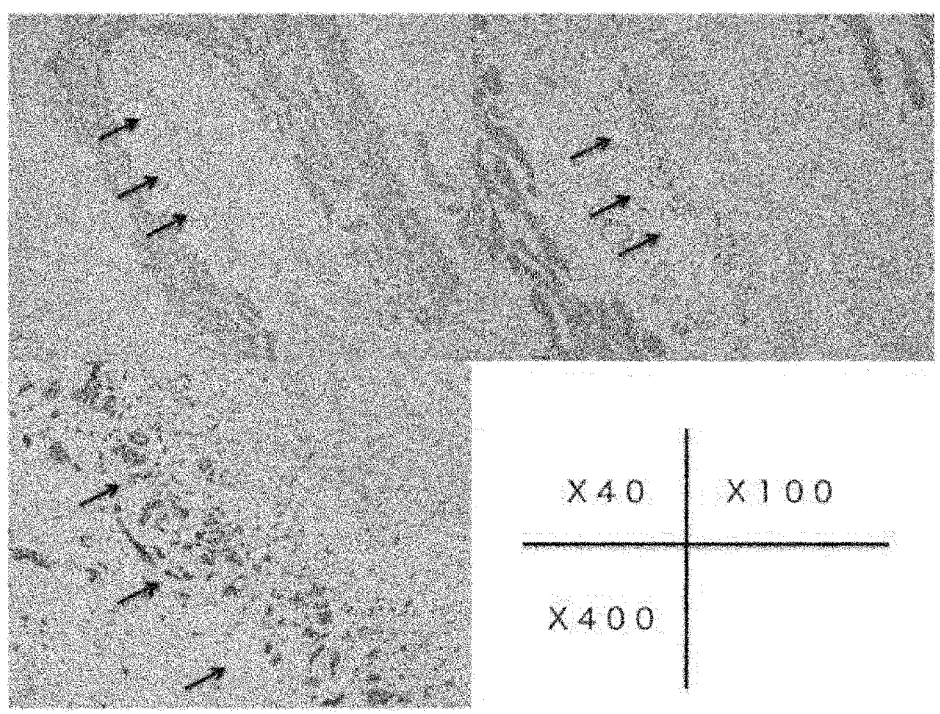
FIG. 17 shows calponin type 1 stain images of ASC injection sites (periurethral zone) of a rat. Magnifications are 40 in the left top, 200 in the right top, and 400 in the left bottom.

In order to confirm that ASC after transplantation was differentiated to smooth muscle cells, ASC (ASC prepared from Green rat subcutaneous fat) was injected into the periurethral zone of a nude rat and evaluated after 28 days in various stain methods. Results are shown in FIGS. 14 to 17. In HE stain, a comparatively differentiated swollen cell clump was observed in the interior of the urethra (FIG. 14, arrows). In addition, muscular tissues stained into red with Masson trichrome stain were observed, corresponding to the swollen sites of the interior of the urethra that was HE stained (FIG. 15, arrows). On the other hand, corresponding to the swollen sites of the interior of the urethra of muscular tissues that were Masson trichrome stained, smooth muscle tissues were shown with αSMA stain and calponin type 1 stain (FIGS. 16 and 17). As described above, the ASC periurethral injection site was shown as a swollen cell clump that was comparatively differentiated in the interior of the urethra. The injection sites were stained as muscular tissues and further stained with αSMA stain with which immature to mature smooth muscle tissues are stained and which reflects smooth muscle tissues, and calponin type 1 stain with which moderately matured smooth muscle tissues are stained; on the other hand, the sites were not stained with MHC (myosin heavy chain) with which matured smooth muscle tissues are stained (no data is shown), and thus, it was presumed that the injected cells are differentiated into smooth muscle tissues and do not reach matured smooth muscle yet.

5. Study of Cytokine Producing Ability of ASC

Figure 18:
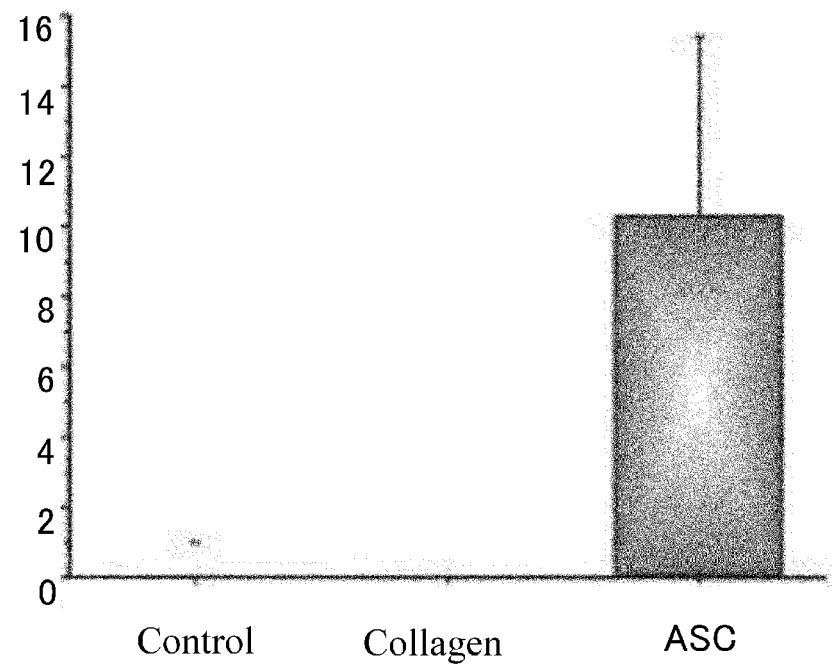
FIG. 18 is a graph showing an HGF concentration in a culture supernatant of human ASC.

Human SVF was collected and subculture was performed (preparation of human ASC). After culturing 6 passages, a medium was replaced with a medium containing 10% FBS and the medium was recovered after 24 hours. A HGF concentration in the medium was measured as well as calculating the cell number. As a result, it was confirmed that about 10 ng of HGF per $10^6$ cells is produced (FIG. 18).

Figure 19:
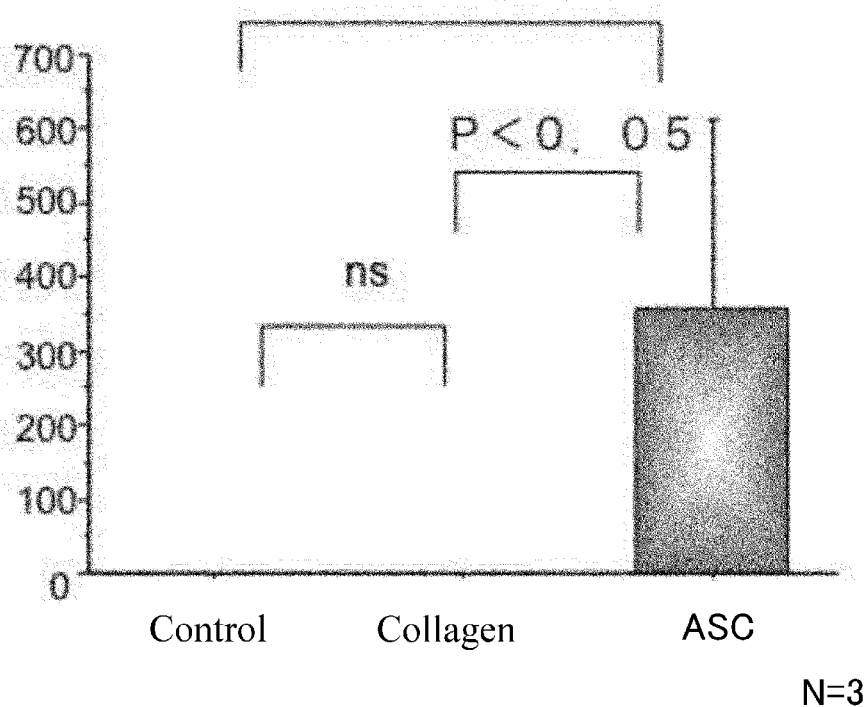
FIG. 19 is a graph showing and a HGF concentration (day 3) of an ASC injection site of a rat. ns: no significant difference.

Then, 3×10⁶ of the above-mentioned cells (human ASC) after subculture were injected into the interior of the urethra wall of a 7 week old female nude rat. Then, the nude rat was sacrificed on day 3, and the HGF (hepatocellular growth factor) concentration of the injection site was measured. As a result, the periurethral tissue concentration of HGF produced from the injected cells reached a peak on day 3 after cell injection (the tissue concentration was about 300 pg per 1 mg) and decreased to the detection limit or less from the next day, day 4 (FIG. 19).

Figure 20:
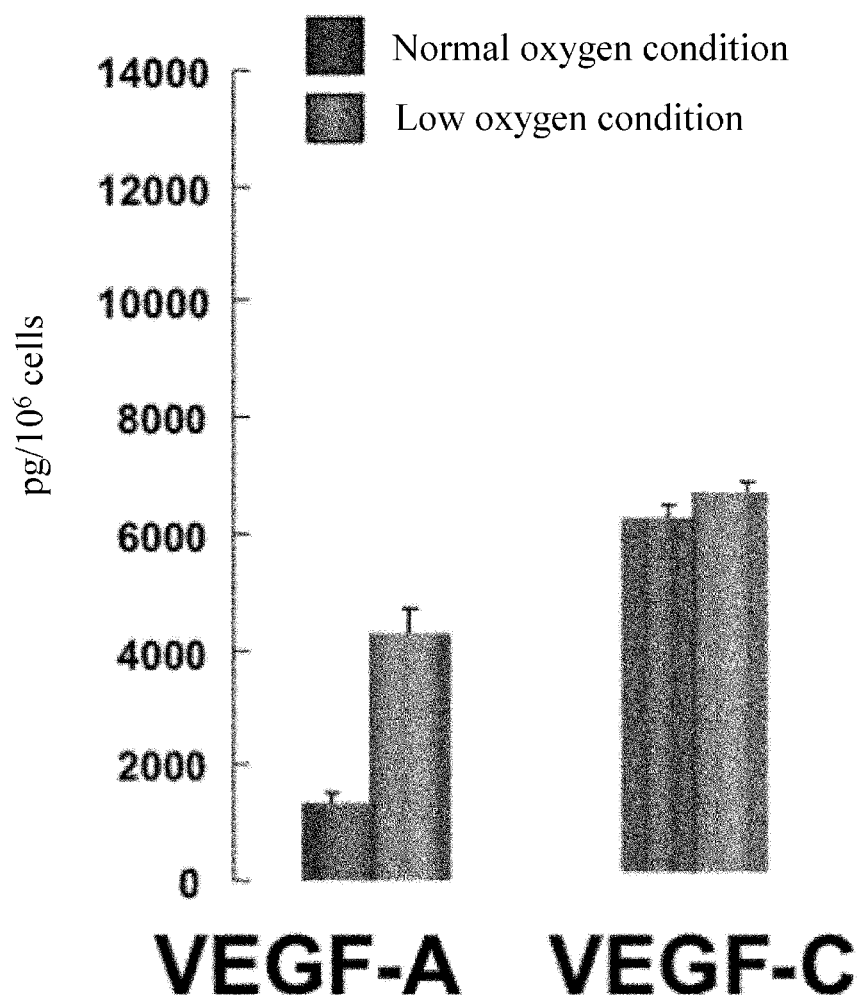
FIG. 20 is a graph showing a VEGF (vascular endothelial growth factor) producing ability of rat adipose tissue-derived SVF (stromal vascular fractions).

On the other hand, SVF separated from rat adipose tissues was cultured (using a medium containing 20% FBS and no growth factor) to measure a VEGF concentration in the culture supernatant. As a result, the VEGF concentration in the culture supernatant was increased under both of the normal oxygen condition and the low oxygen condition (FIG. 20), and it was confirmed that ASC produces VEGF.

As described above, it was confirmed that ASC produces HGF and, at the same time, a HGF concentration in the ASC transplantation site reaches a peak in a few days after transplantation and then disappears. That is, the fact that ASC produces HGF that is supposed to relate to urethral sphincter muscle regrowth and differentiation and have an important role and the fact that a HGF concentration increases only in an early stage of regeneration to guarantee safety were confirmed. In addition, it was confirmed that ASC also produces VEGF.

6. Preclinical Study Using a Large Animal

Autologous ASC was extracted from a subject that was a pig as a large animal with a cell separation device and injected into the periurethral zone. Effectiveness was evaluated in various stain methods after 28 days from cell injection. In addition, safety was also studied.

(1) Injection Operation of Autologous ASC into the Periurethral Zone

The pig was in a supine position under general anesthesia. Bosmin-containing physiological saline (100 ml) was subcutaneously injected in the same procedure as being performed in a clinical use and 100 g of autologous adipose tissues was suctioned with a 18 G subcutaneous fat suction tube. ASC was extracted from the tissues with an ASC separation device (Celution (registered trademark) device) (5 ml solution). Simultaneously, entering the pelvic cavity by lower abdominal median incision (A-1), the bladder neck was peeled and exposed. The cell-containing solution was injected in plurality of times into the peritubular zone at a site of about 2 cm distal from the urethra of the bladder neck. No breeding was confirmed and the surgical site was sutured with a subcutaneous (absorbable thread; Vicryl 3-0) skin (nonabsorbable thread; silken thread 1-0) to complete the operation.

(2) Macroscopic and Microscopic Observations in Periurethral Injection Site on Day 28

Figure 21:
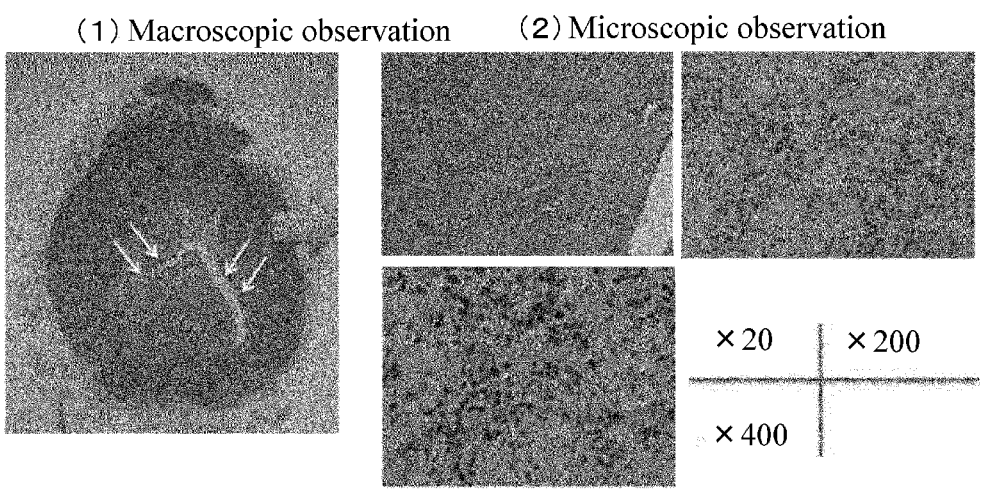
FIG. 21 shows tissue images showing cross sections of an ASC injection site (periurethral zone) of a pig. (1) Macroscopic observation. (2) Microscopic observation: magnifications are 20 in the left top, 200 in the right top, and 400 in the left bottom.

It was observed that the interior of the urethra had a swollen (FIG. 21(1)) fusiform cell structure in the palisade pattern, which corresponded to the injection site (FIG. 21(2)).

(3) Observations of Immunostaining in Injection Site (Day 28)

Figure 22:
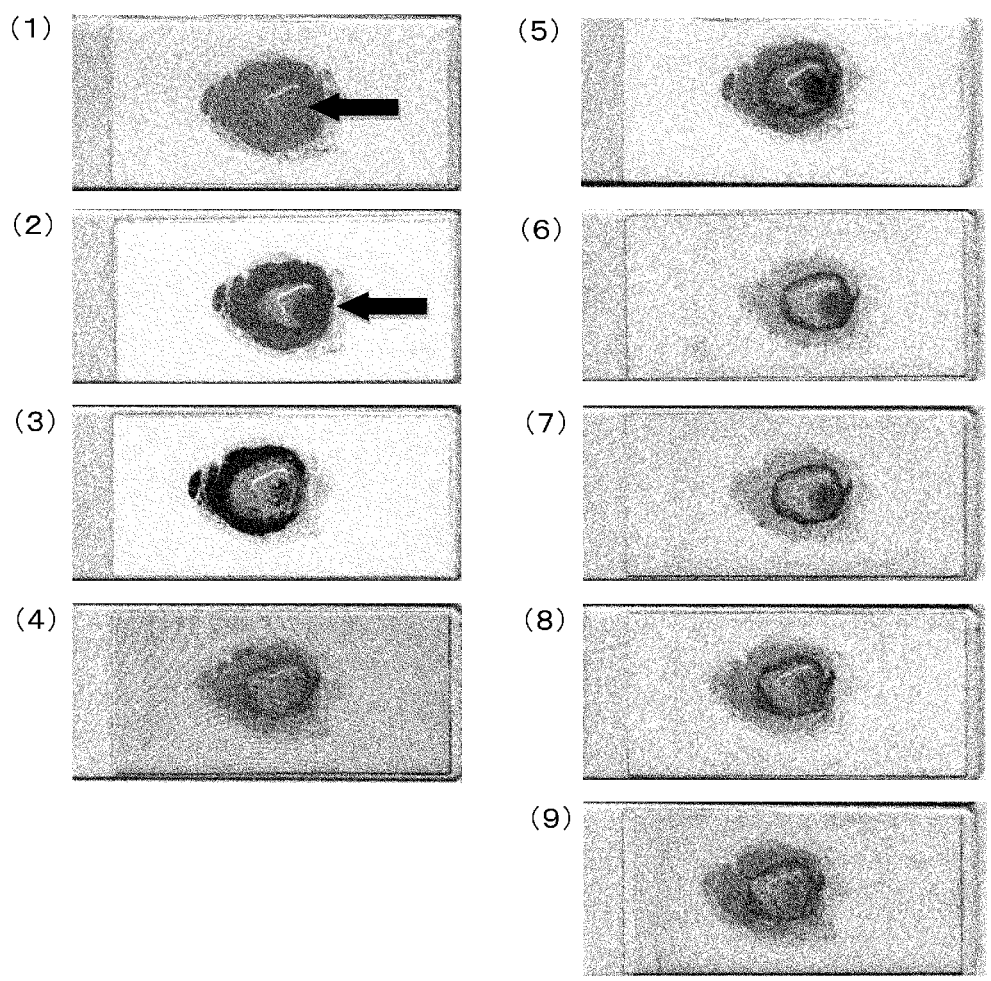
FIG. 22 shows various stain images of ASC injection sites of a pig. (1) HE stain, (2) Masson trichrome stain image, (3) desmin stain image, (4) Ki-67 stain, (5) αSMA stain, (6) calponin type 1 stain, (7) MHC (myosin heavy chain) stain, (8) S-100 stain, (9) synaptophysin stain.

In the HE stain, a swollen, differentiated cell clump is observed in the interior of the urethra (FIG. 22 (1)). As shown by the arrow, muscular tissues that are turned red with Masson trichrome stain were observed, corresponding to a swelling site of the HE stained interior of the urethra (FIG. 22 (2)). A smooth muscle or striated muscle-like structure which is stained with desmin radially from the outside of the swelling site of a Masson trichrome stained muscular tissue component in the interior of the urethra is observed (FIG. 22(3)). Corresponding to the structure, a cell structure stained with Ki-67 that reflects increase of cell proliferation is observed (FIG. 22(4)). The site was stained with three smooth muscle antibodies, αSMA (FIG. 22(5)), calponin type 1 stain (FIG. 22(6)) and MHC (myosin heavy chain) (FIG. 22(7)), which specifically stain smooth muscle tissues. The site was also stained with two antibodies, S-100 (FIG. 22(8)) and synaptophysin (FIG. 22(9)), which reflect nerve cells.

As described above, the ASC periurethral injection site was shown as a matured cell clump that is swollen in the interior of the urethra. The site was stained as a muscular tissue, and further stained with αSMA stain which reflects smooth muscle tissues and stains immature to mature smooth muscle tissues, and calponin type 1 stain which stains moderately matured smooth muscle tissues, and additionally, MHC which stains matured smooth muscle tissues, and the smooth muscle component was stained with the three antibodies. Furthermore, it was presumed that not only smooth muscles but also nerves that are stained with S-100 and synaptophysin, which reflect nerve cells, and control functions are grown in the periphery and the interior. As compared to a small animal, a bump that was projected in the interior of the urethra of a large animal was constituted with smooth muscle cells also on 28 days from cell injection.

(4) Postoperative Progress

Voided urine was shown from the same day of the operation and, no development of a complication of complete urinary retention was observed. Then, voided urine continued smoothly and there was no need for a urethral catheterization treatment. Postoperative general conditions were also preferable and transition of the body weight was from 33.9 to 48.9 kg and increased by 14.1 kg in 28 days (nutritious condition after cell injection; body weight change).

(5) Observations in Blood and Macro and Micro Observations in Major Organs after 28 Days from Cell Injection As a result of a blood test, there were no anemia and malnutrition and abnormality was not observed in peripheral blood and biochemical data. On the other hand, macroscopic observations of extracted organs are as follows and no abnormality was observed.

Skin, muscle; no tumor/inflammation/circulatory disorder

Brain: no abnormality in the color of spinal fluid, no tumor/inflammation/circulatory disorder in brain surface and cut surfaces Pleural cavity: lung; no pleural effusion/adherence/tumor/inflammation, no bleeding/stasis Heart; normal pericardial fluid, no adherent pericardium, no bleeding in epicardium Abdominal cavity: no ascitic fluid/adherence, no tumor/inflammation/circulatory disorder Digestive tract/liver/gallbladder/pancreas/spleen: no tumor/inflammation/circulatory disorder Retroperitoneum organs; for kidney, ureter, bladder, prostate gland, seminal vesicle and penis, including the bladder neck peeled for cell injection and the periurethral zone subjected to cell injection, an observation of a trace of needle injection, adherence, tumor, inflammation, and circulatory disorder was not found.

In addition, microscopic studies on the above described organs were made in HE stain, and an observation that suggests tumor, inflammation, and circulatory disorder was not found.

(6) Summary

Autologous ASC injection operation into the periurethral zone was carried out on a large animal as a subject by an operator who actually performs a treatment in the same method as a clinical study. Complete urinary retention that is a complication of the operation was not developed, and for influence that the cell treatment gave to the entire body, an observation of differentiation of fat, bone and tumor other than the purpose of this clinical regeneration and an observation of inflammation and circulatory disorder were not found in all organs and injection locals. Further, abnormality was not particularly observed also in the blood test. In addition, a bump formed in the injection site was present after 28 days, and effectiveness as a bulking mass was confirmed. Furthermore, differentiation into smooth muscle was shown by immunostaining of a bump formed in the injection site. According to the above description, safety and effectiveness of periurethral ASC injection were shown also in a pig.

7. Study Using an Animal Model Suffering from Urinary Incontinence

Using an ECM model rat (rat having stress urinary incontinence, whose periurethral zone of the prostate gland was peeled off with an electric knife; Chermansky C. J. et al. Neurourology and Urodynamics 23: 166-171 (2004)), which has been known for an animal model reproducing a condition of intractable stress urinary incontinence after prostate gland extirpation in a human, a therapeutic effect of an operation of ASC injection into the periurethral zone was examined. Firstly, according to a reported method, the periurethral zone of the prostate gland of a male wistar rat (250-300 g) was peeled off, and then ASC that has been previously prepared (prepared from subcutaneous fat of the same rat in a method described in WO/2008/018450 (PCT/JP2007/065431)) was injected (ASC treated group). For a control, a solvent (DMEM medium) was injected in place of ASC (ECM model group). After 2 weeks and 4 weeks from the operations, the ASC treated group, the ECM model group and the sham operation group (sham group) were compared for evaluation.

Figure 23:
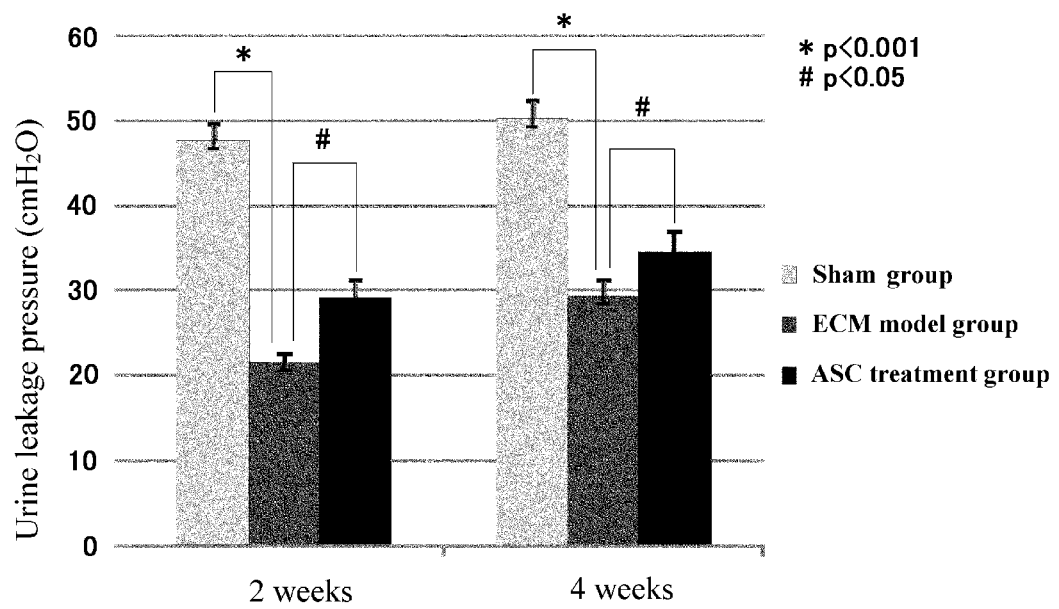
FIG. 23 is a graph showing therapeutic effects by ASC periurethral injection into an ECM model rat. Urine leakage pressures of an ASC treatment group, an ECM model group and a sham operation group (sham group) after 2 weeks and 4 weeks from the operation were compared for evaluation. The sham operation group, ECM model group, and ASC treatment group in order from the left. *$p<0.001$, #$p<0.05$

The evaluation results are shown in FIG. 23. In the ASC treated group, a urine leakage pressure was significantly high as compared to the ECM model group. In addition, rise in the urine leakage pressure with time was also observed. Thus, an effect of improving urinary incontinence due to adipose tissue derived stem cell injection into the periurethral zone in intractable stress urinary incontinence cases after prostate gland cancer operation was observed also in a basic experiment having constant conditions.

INDUSTRIAL APPLICABILITY

The cell preparation of the present invention is used for improvement of erectile dysfunction or recovery of the urge to urinate (recovery of sensory disorders of the lower urinary tract). For a subject (patient) to which the cell preparation of the present invention is applied, a patient suffering from stress urinary incontinence, a patient suffering from sensory disorders of the lower urinary tract after a prostate gland operation, a patient suffering from urine collection disorder, a patient suffering from erectile dysfunction, and the like are assumed.

The invention is not limited by description of the embodiments and examples of the invention described above at all. Various modified embodiments are also included in the invention within the range that a person skilled in the art can easily conceive of, without departing from the description of the scope of patent claims.

Contents of treatises, unexamined patent publications, and examined patent publications specified in this specification are all incorporated herein by their references.

The invention claimed is:

1. A method of treating sensory disorders of the lower urinary tract, comprising administering a cell preparation comprising human adipose tissue-derived mesenchymal stem cells to the external urethral sphincter muscle and/or to the membranous urethra of external urethral sphincter muscle of a patient suffering from sensory disorders of the lower urinary tract.

2. A method of treating sensory disorders of the lower urinary tract, comprising administering a therapeutically effective amount of adipose tissue-derived mesenchymal stem cells to the external urethral sphincter muscle and/or to the membranous urethra of external urethral sphincter muscle of a patient suffering from sensory disorders of the lower urinary tract.

3. A method of treating sensory disorders of the lower urinary tract, comprising administering therapeutically effective amounts of adipose tissue-derived mesenchymal stem cells and body fat to the external urethral sphincter muscle and/or to the membranous urethra of external urethral sphincter muscle of a patient suffering from sensory disorders of the lower urinary tract.

* * * * *